(12) United States Patent
Miller et al.

(10) Patent No.: US 12,343,042 B2
(45) Date of Patent: Jul. 1, 2025

(54) PERICARDIAL PUNCTURE DEVICE AND METHOD

(71) Applicant: Boston Scientific Medical Device Limited, Galway (IE)

(72) Inventors: Brock Miller, Toronto (CA); Matthew Gravett, Milton (CA); Kai-Lon Fok, Mississauga (CA)

(73) Assignee: Boston Scientific Medical Device Limited, Galway (IE)

(*) Notice: Subject to any disclaimer, the term of this patent is extended or adjusted under 35 U.S.C. 154(b) by 926 days.

(21) Appl. No.: 17/375,382

(22) Filed: Jul. 14, 2021

(65) Prior Publication Data

US 2022/0015804 A1    Jan. 20, 2022

Related U.S. Application Data

(60) Provisional application No. 63/052,692, filed on Jul. 16, 2020.

(51) Int. Cl.
*A61B 17/34* (2006.01)

(52) U.S. Cl.
CPC ...... *A61B 17/3496* (2013.01); *A61B 17/3423* (2013.01); *A61B 2017/3425* (2013.01)

(58) Field of Classification Search
CPC ........ A61M 25/0102; A61M 2210/122; A61M 25/0606; A61M 25/0612; A61M 25/0625; A61M 25/0113; A61M 25/06; A61M 25/065; A61M 25/0089; A61B 17/34; A61B 17/3401; A61B 17/32053; A61B 17/3496; A61B 17/3423; A61B 17/3478; A61B 2017/3409; A61B 2017/3425; A61B 2017/00247
See application file for complete search history.

(56) References Cited

U.S. PATENT DOCUMENTS

| 175,254 | A | 3/1876 | Oberly |
| 827,626 | A | 7/1906 | Gillet |
| 848,711 | A | 4/1907 | Weaver |
| 1,072,954 | A | 9/1913 | Junn |

(Continued)

FOREIGN PATENT DOCUMENTS

WO    WO-2018083599 A1 *  5/2018  ......... A61B 17/3205

*Primary Examiner* — Courtney B Fredrickson
*Assistant Examiner* — Kayla M. Turkowski
(74) *Attorney, Agent, or Firm* — Nelson Mullins Riley & Scarborough

(57) ABSTRACT

A pericardial puncture device includes an introducer, a needle, and an actuator. The introducer has a lumen and extends between an introducer proximal portion defining an introducer proximal end and an introducer distal portion defining an introducer distal end. The needle is received in the lumen and extends between a needle proximal portion and a needle distal portion having a sharp distal tip. The needle is movable from a retracted configuration to an advanced configuration. In the retracted configuration, the sharp distal tip is within the lumen and shy of the introducer distal end. In the advanced configuration, the sharp distal tip outside of the lumen and proud of the introducer distal end. The actuator includes a handle that is rotatable in a first direction with respect to the introducer to drive movement of the needle from the retracted configuration towards the advanced configuration.

15 Claims, 3 Drawing Sheets

(56) References Cited

U.S. PATENT DOCUMENTS

| | | | |
|---|---|---|---|
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |
| 4,129,129 | A | 12/1978 | Amrine |
| 4,244,362 | A | 1/1981 | Anderson |
| 4,401,124 | A | 8/1983 | Guess et al. |
| 4,639,252 | A | 1/1987 | Kelly et al. |
| 4,641,649 | A | 2/1987 | Walinsky et al. |
| 4,669,467 | A | 6/1987 | Willett et al. |
| 4,682,596 | A | 7/1987 | Bales et al. |
| 4,790,311 | A | 12/1988 | Ruiz |
| 4,790,809 | A | 12/1988 | Kuntz |
| 4,793,350 | A | 12/1988 | Mar et al. |
| 4,807,620 | A | 2/1989 | Strul et al. |
| 4,832,048 | A | 5/1989 | Cohen |
| 4,840,622 | A | 6/1989 | Hardy |
| 4,863,441 | A | 9/1989 | Lindsay et al. |
| 4,884,567 | A | 12/1989 | Elliott et al. |
| 4,892,104 | A | 1/1990 | Ito et al. |
| 4,896,671 | A | 1/1990 | Cunningham et al. |
| 4,928,693 | A | 5/1990 | Goodin et al. |
| 4,936,281 | A | 6/1990 | Stasz |
| 4,960,410 | A | 10/1990 | Pinchuk |
| 4,977,897 | A | 12/1990 | Hurwitz |
| 4,998,933 | A | 3/1991 | Eggers et al. |
| 5,006,119 | A | 4/1991 | Acker et al. |
| 5,019,076 | A | 5/1991 | Yamanashi et al. |
| 5,047,026 | A | 9/1991 | Rydell |
| 5,081,997 | A | 1/1992 | Bosley et al. |
| 5,098,431 | A | 3/1992 | Rydell |
| 5,112,048 | A | 5/1992 | Kienle |
| 5,154,724 | A | 10/1992 | Andrews |
| 5,195,506 | A * | 3/1993 | Hulfish .............. A61B 17/0218 600/206 |
| 5,201,756 | A | 4/1993 | Horzewski et al. |
| 5,209,741 | A | 5/1993 | Spaeth |
| 5,211,183 | A | 5/1993 | Wilson |
| 5,221,256 | A | 6/1993 | Mahurkar |
| 5,230,349 | A | 7/1993 | Langberg |
| 5,281,216 | A | 1/1994 | Klicek |
| 5,300,068 | A | 4/1994 | Rosar et al. |
| 5,300,069 | A | 4/1994 | Hunsberger et al. |
| 5,314,418 | A | 5/1994 | Takano et al. |
| 5,318,525 | A | 6/1994 | West et al. |
| 5,327,905 | A | 7/1994 | Avitall |
| 5,364,393 | A | 11/1994 | Auth et al. |
| 5,372,596 | A | 12/1994 | Klicek et al. |
| 5,380,304 | A | 1/1995 | Parker |
| 5,397,304 | A | 3/1995 | Truckai |
| 5,403,338 | A | 4/1995 | Milo |
| 5,423,809 | A | 6/1995 | Klicek |
| 5,425,382 | A | 6/1995 | Golden et al. |
| 5,490,859 | A | 2/1996 | Mische et al. |
| 5,497,774 | A | 3/1996 | Swartz et al. |
| 5,507,751 | A | 4/1996 | Goode et al. |
| 5,509,411 | A | 4/1996 | Littmann et al. |
| 5,540,681 | A | 7/1996 | Strul et al. |
| 5,545,200 | A | 8/1996 | West et al. |
| 5,555,618 | A | 9/1996 | Winkler |
| 5,571,088 | A | 11/1996 | Lennox et al. |
| 5,575,766 | A | 11/1996 | Swartz et al. |
| 5,575,772 | A | 11/1996 | Lennox |
| 5,599,347 | A | 2/1997 | Hart et al. |
| 5,605,162 | A | 2/1997 | Mirzaee et al. |
| 5,617,878 | A | 4/1997 | Taheri |
| 5,622,169 | A | 4/1997 | Golden et al. |
| 5,624,430 | A | 4/1997 | Eton et al. |
| 5,667,488 | A | 9/1997 | Lundquist et al. |
| 5,673,695 | A | 10/1997 | McGee et al. |
| 5,674,208 | A | 10/1997 | Berg et al. |
| 5,683,366 | A | 11/1997 | Eggers et al. |
| 5,720,744 | A | 2/1998 | Eggleston et al. |
| 5,741,249 | A | 4/1998 | Moss et al. |
| 5,766,135 | A | 6/1998 | Terwilliger |
| 5,779,688 | A | 7/1998 | Imran et al. |
| 5,810,764 | A | 9/1998 | Eggers et al. |
| 5,814,028 | A | 9/1998 | Swartz et al. |
| 5,830,214 | A | 11/1998 | Flom et al. |
| 5,836,875 | A | 11/1998 | Webster, Jr. |
| 5,849,011 | A | 12/1998 | Jones et al. |
| 5,851,210 | A | 12/1998 | Torossian |
| 5,885,227 | A | 3/1999 | Finlayson |
| 5,888,201 | A | 3/1999 | Stinson et al. |
| 5,893,848 | A | 4/1999 | Negus et al. |
| 5,893,885 | A | 4/1999 | Webster, Jr. |
| 5,904,679 | A | 5/1999 | Clayman |
| 5,916,210 | A | 6/1999 | Winston |
| 5,921,957 | A | 7/1999 | Killion et al. |
| 5,931,818 | A | 8/1999 | Werp et al. |
| 5,944,023 | A | 8/1999 | Johnson et al. |
| 5,951,482 | A | 9/1999 | Winston et al. |
| 5,957,842 | A | 9/1999 | Littmann et al. |
| 5,964,757 | A | 10/1999 | Ponzi |
| 5,967,976 | A | 10/1999 | Larsen et al. |
| 5,989,276 | A | 11/1999 | Houser et al. |
| 6,007,555 | A | 12/1999 | Devine |
| 6,009,877 | A | 1/2000 | Edwards |
| 6,013,072 | A | 1/2000 | Winston et al. |
| 6,017,340 | A | 1/2000 | Cassidy et al. |
| 6,018,676 | A | 1/2000 | Davis et al. |
| 6,019,776 | A * | 2/2000 | Preissman .......... A61B 17/8811 604/165.01 |
| 6,030,380 | A | 2/2000 | Auth et al. |
| 6,032,674 | A | 3/2000 | Eggers et al. |
| 6,048,349 | A | 4/2000 | Winston et al. |
| 6,053,870 | A | 4/2000 | Fulton, III |
| 6,053,904 | A | 4/2000 | Scribner et al. |
| 6,056,747 | A | 5/2000 | Saadat et al. |
| 6,063,093 | A | 5/2000 | Winston et al. |
| 6,093,185 | A | 7/2000 | Ellis et al. |
| 6,106,515 | A | 8/2000 | Winston et al. |
| 6,106,520 | A | 8/2000 | Laufer et al. |
| 6,117,131 | A | 9/2000 | Taylor |
| 6,142,992 | A | 11/2000 | Cheng et al. |
| 6,146,380 | A | 11/2000 | Racz et al. |
| 6,155,264 | A | 12/2000 | Ressemann et al. |
| 6,156,031 | A | 12/2000 | Aita et al. |
| 6,171,305 | B1 | 1/2001 | Sherman |
| 6,179,824 | B1 | 1/2001 | Eggers et al. |
| 6,193,676 | B1 | 2/2001 | Winston et al. |
| 6,193,715 | B1 | 2/2001 | Wrublewski et al. |
| 6,210,408 | B1 | 4/2001 | Chandrasekaran et al. |
| 6,217,575 | B1 | 4/2001 | Devore et al. |
| 6,221,061 | B1 | 4/2001 | Engelson et al. |
| 6,228,076 | B1 | 5/2001 | Winston et al. |
| 6,245,054 | B1 | 6/2001 | Fuimaono et al. |
| 6,267,758 | B1 | 7/2001 | Daw et al. |
| 6,283,983 | B1 | 9/2001 | Makower et al. |
| 6,292,678 | B1 | 9/2001 | Hall et al. |
| 6,293,945 | B1 | 9/2001 | Parins et al. |
| 6,296,615 | B1 | 10/2001 | Brockway et al. |
| 6,296,636 | B1 | 10/2001 | Cheng et al. |
| 6,302,898 | B1 | 10/2001 | Edwards et al. |
| 6,304,769 | B1 | 10/2001 | Arenson et al. |
| 6,315,777 | B1 | 11/2001 | Comben |
| 6,328,699 | B1 | 12/2001 | Eigler et al. |
| 6,360,128 | B2 | 3/2002 | Kordis et al. |
| 6,364,877 | B1 | 4/2002 | Goble et al. |
| 6,385,472 | B1 | 5/2002 | Hall et al. |
| 6,394,976 | B1 | 5/2002 | Winston et al. |
| 6,395,002 | B1 | 5/2002 | Ellman et al. |
| 6,419,674 | B1 | 7/2002 | Bowser et al. |
| 6,428,551 | B1 | 8/2002 | Hall et al. |
| 6,450,989 | B2 | 9/2002 | Dubrul et al. |
| 6,475,214 | B1 | 11/2002 | Moaddeb |
| 6,485,485 | B1 | 11/2002 | Winston et al. |
| 6,508,754 | B1 | 1/2003 | Liprie et al. |
| 6,524,303 | B1 | 2/2003 | Garibaldi |

(56) References Cited

U.S. PATENT DOCUMENTS

| | | |
|---|---|---|
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2009/0275970 A1* | 11/2009 | Leibowitz .......... A61B 17/3496 606/185 |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0276001 A1* | 11/2011 | Schultz .............. A61B 17/3415 604/164.01 |
| 2012/0232546 A1 | 9/2012 | Mirza et al. |
| 2012/0265055 A1 | 10/2012 | Melsheimer et al. |
| 2012/0330156 A1 | 12/2012 | Brown et al. |

(56) References Cited

U.S. PATENT DOCUMENTS

| | | |
|---|---|---|
| 2012/0330320 A1* | 12/2012 | Takizawa ............ A61B 17/8816 606/94 |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2013/0345798 A1* | 12/2013 | Jimenez ............ A61M 25/0136 623/2.11 |
| 2014/0206987 A1 | 7/2014 | Urbanski et al. |
| 2014/0276894 A1* | 9/2014 | Ramsay ............. A61B 17/8897 606/104 |
| 2014/0296769 A1 | 10/2014 | Hyde et al. |
| 2016/0220741 A1 | 8/2016 | Garrison et al. |
| 2018/0117263 A1* | 5/2018 | Cumbo ............... A61M 5/3287 |
| 2019/0021763 A1 | 1/2019 | Zhou et al. |
| 2019/0247035 A1 | 8/2019 | Gittard et al. |

* cited by examiner

1

PERICARDIAL PUNCTURE DEVICE AND METHOD

FIELD

This document relates to medical devices. More specifically, this document relates to devices for pericardial puncture, and related methods.

SUMMARY

The following summary is intended to introduce the reader to various aspects of the detailed description, but not to define or delimit any invention.

Pericardial puncture devices are disclosed. According to some aspects, a pericardial puncture device includes an introducer extending along a longitudinal axis between an introducer proximal portion defining an introducer proximal end and an introducer distal portion defining an introducer distal end. The introducer has an introducer lumen extending between the introducer proximal end and the introducer distal end. A needle is received in the introducer lumen and extends between a needle proximal portion and a needle distal portion having a sharp distal tip. The needle is movable from a retracted configuration to an advanced configuration. In the retracted configuration, the sharp distal tip is within the lumen and shy of the introducer distal end. In the advanced configuration, the sharp distal tip is outside of the lumen and proud of (i.e. extended slightly beyond, projecting slightly out of, slightly distal to) the introducer distal end. An actuator is mounted to the introducer proximal portion and is engaged with the needle proximal portion. The actuator includes a handle that is rotatable in a first direction with respect to the introducer to drive movement of the needle from the retracted configuration towards the advanced configuration.

In some examples, the actuator includes a lead screw mounted to the handle. The lead screw can be received in the introducer proximal portion and the handle can extend proud of the introducer proximal portion. Rotation of the handle in the first direction can drive rotation of the lead screw in the first direction.

In some examples, the needle proximal portion includes a lead nut. The lead screw can be received in and engaged with the lead nut to drive movement of the needle from the retracted configuration to the advanced configuration by rotation of the handle.

In some examples, the handle is rotatable about the longitudinal axis of the introducer.

In some examples, the actuator is longitudinally fixed with respect to the introducer.

In some examples, at least a section of the introducer distal portion is radiopaque.

In some examples the introducer distal end is blunt.

In some examples the handle is further rotatable in a second direction with respect to the introducer to drive movement of the needle from the advanced configuration towards the retracted configuration.

In some examples the introducer proximal portion comprises an internal circumferential groove, and the handle comprises an outer circumferential tongue. The tongue can be received in the groove to longitudinally fix the actuator with respect to the introducer.

In some examples, the introducer includes a metallic hypotube embedded in a polymeric shaft. The metallic hypotube can be a stainless steel or nitinol hypotube and the polymeric shaft can be a high-density polyethylene shaft.

2

In some examples, the introducer has a length of at least 5 inches.

In some examples the needle is of a one-piece construction. The needle can be fabricated from stainless steel.

Methods for puncturing a pericardium are also disclosed. According to some aspects, a method for puncturing a pericardium includes: a. with a needle received in a lumen of an introducer and a sharp distal tip of the needle shrouded within the introducer, advancing the introducer towards a pericardium; and b. rotating a handle of an actuator in a first direction to advance the sharp distal tip out of the introducer and puncture the pericardium.

In some examples, in step b., the longitudinal position of the actuator is fixed with respect to the introducer.

In some examples, in step b., rotation of the handle causes rotation of a lead screw of the actuator, and rotation of the lead screw causes advancement of a lead nut of the needle.

In some examples, the method further includes, prior to step b., using fluoroscopy to confirm the position of the introducer or the sharp distal tip.

In some examples, rotating the handle of the actuator in the first direction includes rotating the handle about a longitudinal axis of the introducer.

According to some additional aspects, a pericardial puncture device includes an introducer extending along a longitudinal axis between an introducer proximal portion defining an introducer proximal end and an introducer distal portion defining an introducer distal end. The introducer has an introducer lumen extending between the introducer proximal end and the introducer distal end. An actuator is mounted to the introducer. The actuator includes a lead screw that is received in the introducer proximal portion and a handle that extends proud of the introducer proximal portion. The actuator is rotatable about the longitudinal axis with respect to the introducer and is longitudinally fixed with respect to the introducer. A needle extends along the longitudinal axis between a needle proximal portion having a lead nut and a needle distal portion having a sharp distal tip. The lead screw is received in and engaged with the lead nut. Rotation of the actuator about the longitudinal axis in a first direction drives longitudinal advancement of the needle to position the sharp distal tip proud of the introducer distal end, and rotation of the actuator about the longitudinal axis in a second direction opposite the first direction drives longitudinal retraction of the needle to position the sharp distal tip shy of the introducer distal end.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are devices that can be used to puncture tissue, such as the pericardium (e.g. in order to gain access to the epicardium). The devices can generally include a needle, which can be used to puncture tissue, and an introducer, which can guide the needle to the tissue. The devices are generally configured to allow for relatively fine adjustments of the position of the needle with respect to the introducer. This can provide greater user control, and in the case of pericardial puncture, can prevent or minimize the risk of puncturing deeper tissues of the heart with the needle, such as the epicardium.

Figures 1, 2:
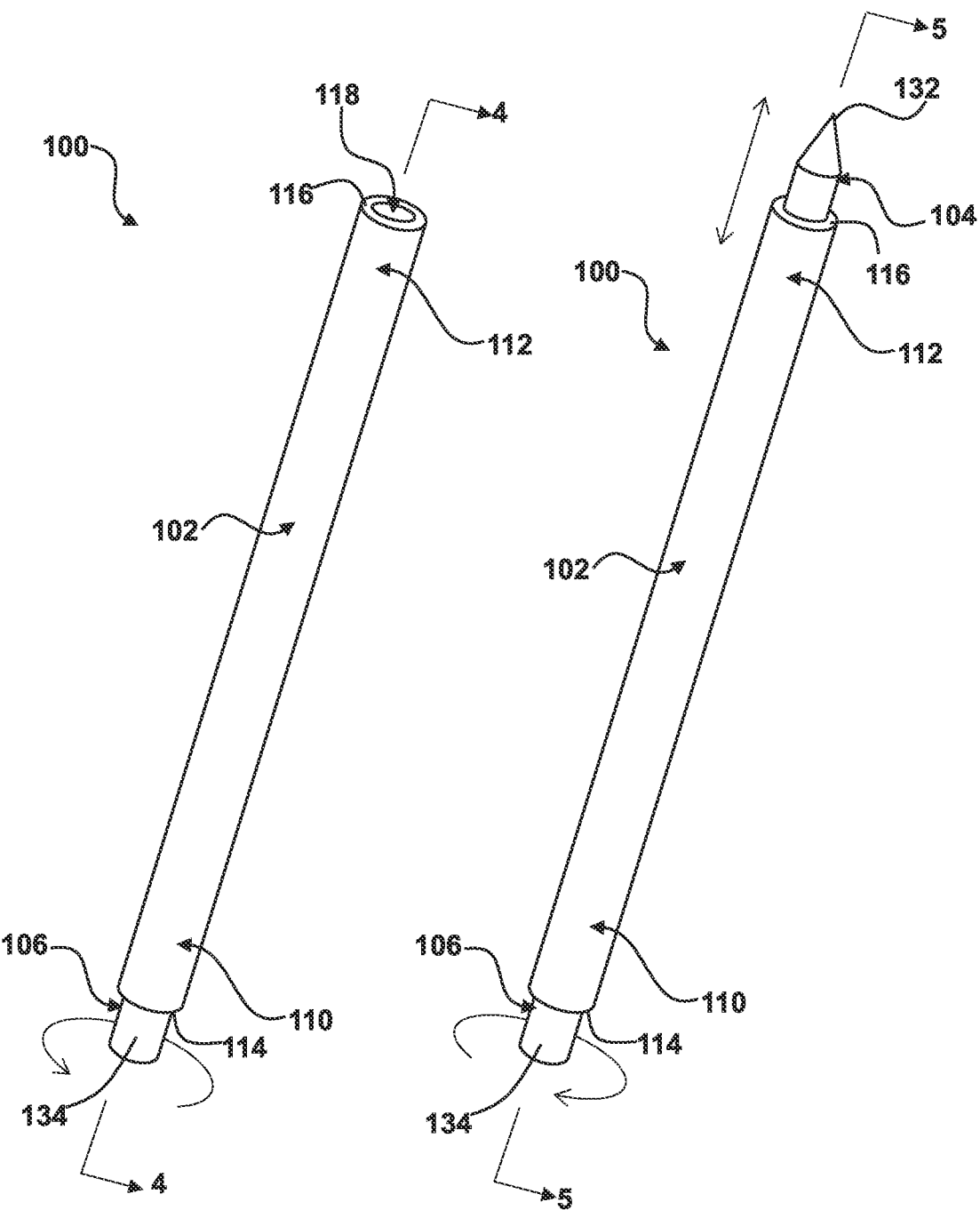
FIG. 1 is a perspective view of an example pericardial puncture device, with a needle thereof in a retracted configuration.
FIG. 2 is a perspective view of the pericardial puncture device of FIG. 1, with the needle thereof in an advanced configuration.

Referring now to FIGS. 1 and 2, an example pericardial puncture device 100 is shown. In the example shown, the pericardial puncture device 100 includes an introducer 102, a needle 104 (not visible in FIG. 1), and an actuator 106. In FIG. 1, the needle 104 is shown in a retracted configuration, and in FIG. 2, the needle 104 is shown in an advanced configuration. The needle 104 can be moved longitudinally between the retracted and advanced configurations by rotation of the actuator 106, as will be described in further detail below.

Figure 3:
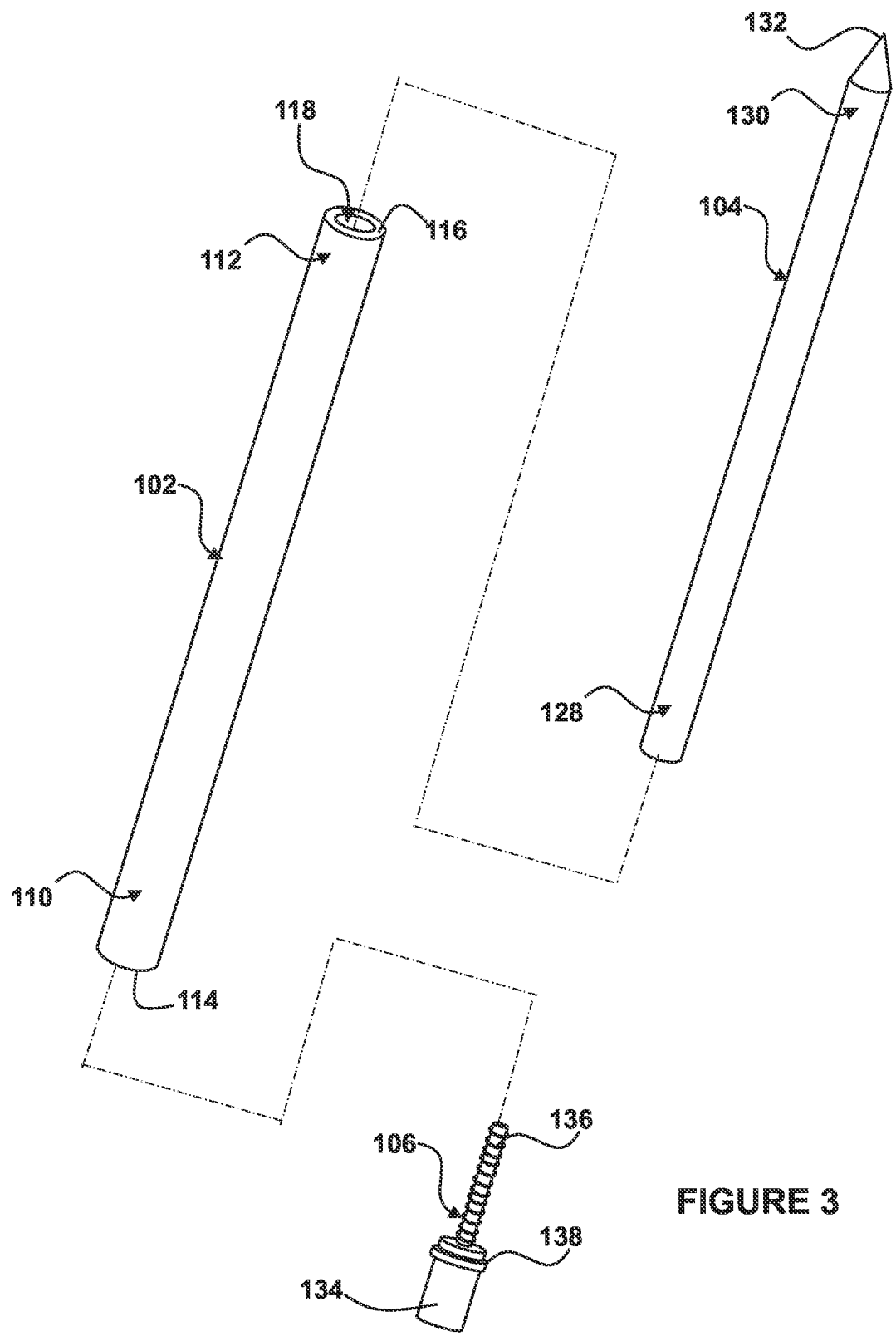
FIG. 3 is an exploded perspective view of the pericardial puncture device of FIGS. 1 and 2.

Referring to FIG. 3, in the example shown, the introducer 102 is generally in the form of an elongate tube. The introducer 102 extends along a longitudinal axis 108 (shown in FIGS. 4 and 5) between a proximal portion 110 (also referred to herein as an 'introducer proximal portion') and a distal portion 112 (also referred to herein as an 'introducer distal portion'). The proximal portion 110 defines a proximal end 114 of the introducer 102 (also referred to herein as an 'introducer proximal end'), and the distal portion 112 defines a distal end 116 of the introducer 102 (also referred to herein as an 'introducer distal end'). The distal end 116 is blunt, in order to prevent damage to tissue (e.g. the pericardium) when the distal end 116 contacts tissue. The introducer 102 has a lumen 118, (also referred to herein as an 'introducer lumen'), which extends between the proximal end 114 and the distal end 116. As used herein, the term 'proximal' refers to the end that in use is intended to be closest to or proximate the user, and the term 'distal' refers to the end that in use is intended to be closest to or proximate the patient.

Figure 4:
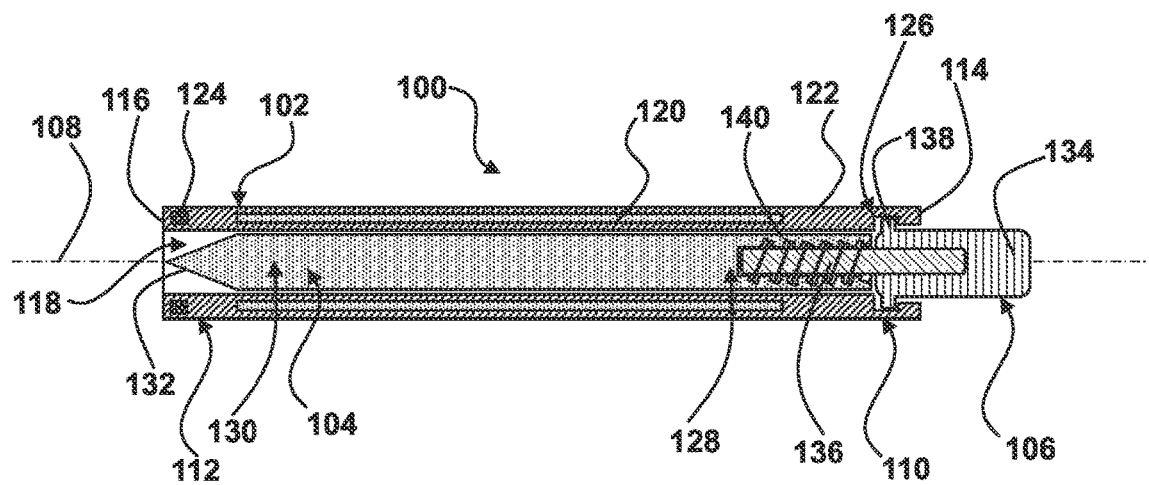
FIG. 4 is a schematic cross-section taken along line 4-4 in FIG. 1.
Figure 5:
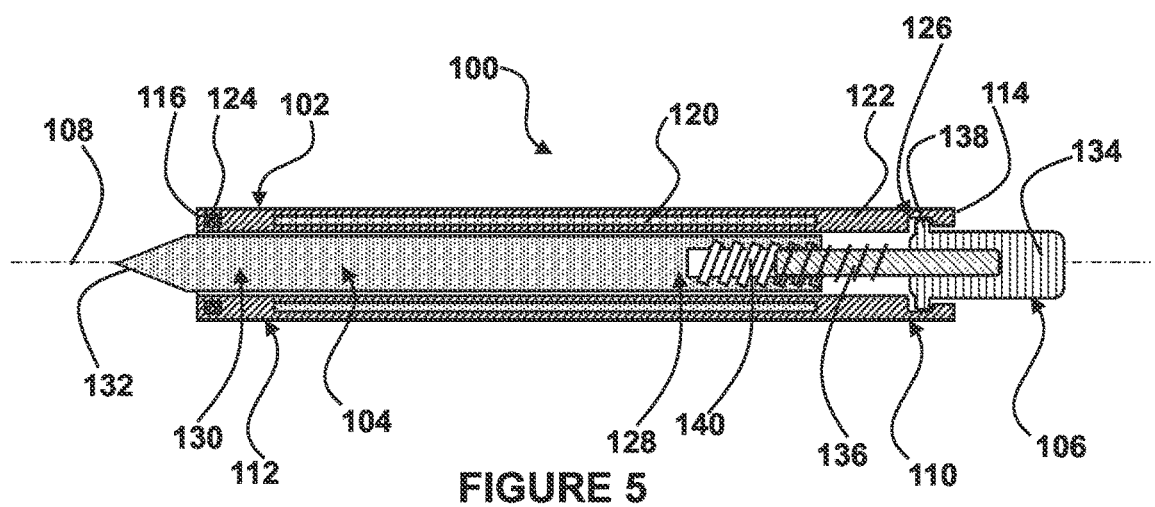
FIG. 5 is a schematic cross-section taken along line 5-5 in FIG. 2.

Referring to FIGS. 4 and 5, in the example shown, the introducer 102 includes a metallic hypotube 120 that is embedded in a polymeric shaft 122. The metallic hypotube 120 can be, for example, a stainless steel or nitinol hypotube. The polymeric shaft 122 can be, for example, a high-density polyethylene (HDPE) shaft, or a shaft of another lubricious polymer.

Referring still to FIGS. 4 and 5, at least a section of the introducer distal portion 112 can be radiopaque, to allow for visualization of the introducer 102 under fluoroscopy. In the example shown, the introducer distal portion 112 includes a radiopaque band 124 that is embedded in the polymeric shaft 122. The radiopaque band 124 can be, for example, a platinum or iridium band or coil. Alternatively, a portion of the polymeric shaft can include a radiopaque filler.

Referring still to FIGS. 4 and 5, the introducer proximal portion 110 includes an internal circumferential groove 126, which as described in further detail below engages the actuator 106 to fix the longitudinal position of the actuator 106 with respect to the introducer 102.

The introducer 102 can have a length of, for example, greater than or equal to about 5 inches (e.g. between about 5 inches and about 10 inches).

Referring back to FIG. 3, the needle 104 extends between a proximal portion 128 (also referred to herein as a 'needle proximal portion') and a distal portion 130 (also referred to herein as a 'needle distal portion'). The needle distal portion 130 has a sharp distal tip 132, which can puncture tissue (e.g. the pericardium). The needle 104 can be, for example, a metallic shaft (e.g. a stainless steel shaft) that is machined to have a sharp tip. The distal tip 132 can have various different profiles, such as beveled or conical. The needle 104 can optionally have an inner lumen (not shown) to facilitate delivery or aspiration of fluids (e.g. delivery of contrast agent or aspiration of blood).

In use, the needle 104 is received in (otherwise referred to as 'cannulated in') the introducer lumen 118 and is movable between a retracted configuration (shown in FIGS. 1 and 4) and an advanced configuration (shown in FIGS. 2 and 5). In the advanced configuration, the needle 104 is longitudinally advanced (i.e. moved distally) with respect to the introducer 102 to position the sharp distal tip 132 outside of the lumen 118 and proud of the introducer distal end 116. When the sharp distal tip 132 is outside of the lumen 118, the needle 104 can puncture tissue. In the retracted configuration, the needle 104 is longitudinally retracted (i.e. moved proximally) with respect to the introducer 102 to position the sharp distal tip 132 within the lumen 118 and shy of the introducer distal end 116. When the needle 104 is in the retracted configuration, tissue is protected from the sharp distal tip 132.

As mentioned above, the device 100 is configured to allow for relatively slow and controlled movement of the needle 104 from the retracted configuration to the advanced configuration, to allow for relatively slow and controlled puncture of tissue as the needle 104 moves towards the advanced configuration. This can allow for enhanced patient safety. In the example shown, the device 100 is configured so that the actuator 106 serves as a lead screw, the needle 104 serves as a lead nut, and rotation of the actuator 106 causes longitudinal movement of the needle 104. More specifically, referring to FIG. 3, the actuator 106 includes a handle 134 and a lead screw 136 mounted to and extending longitudinally from the handle 134. The handle 134 includes an outer circumferential tongue 138. Referring to FIGS. 4 and 5, the actuator 106 is mounted to the proximal portion 110 of the introducer 102 so that the lead screw 136 is received in the proximal portion 110 of the introducer 102 and the handle 134 extends proud of the proximal portion 110 of the introducer 102. Furthermore, the tongue 138 is received in the groove 126 to longitudinally fix the actuator 106 with respect to the introducer 102, while allowing for rotation of the actuator 106 about the longitudinal axis 108 with respect to the introducer 102.

Referring still to FIGS. 4 and 5, the proximal portion 128 of the needle 104 includes a lead nut 140. In the example shown, the needle 104 is of a one-piece construction and the lead nut 140 is integral with the remainder of the needle 104. For example, the lead nut 140 can be formed by machining the metallic shaft of the needle 104. In alternative examples, the lead nut may be a separate piece that is affixed to the remainder of the needle.

Referring still to FIGS. 4 and 5, the actuator 106 is engaged with the needle proximal portion 128 so that the lead screw 136 is received in and engaged with the lead nut 140, to drive advancement and retraction of the needle 104 by rotation of the handle 134. Rotation of the handle 134 in a first direction (e.g. clockwise) with respect to the introducer 102 drives rotation of the lead screw 136 in the first direction, which drives longitudinal advancement of the needle 104 (i.e. movement towards the advanced position, as shown in FIG. 5). Rotation of the handle 134 in a second direction (e.g. counter-clockwise) with respect to the introducer 102 drives rotation of the lead screw 136 in the second direction, which drives longitudinal retraction of the needle 104 (i.e. movement towards the retracted position, as show in FIG. 4).

The device 100 may have various uses and may be used according to various methods; however, the device 100 may be particularly useful in pericardial puncture. For example, the device 100 may be used to puncture a pericardium by percutaneously advancing the introducer 102 towards the pericardium with the needle 104 received in the lumen 118 and with the sharp distal tip 132 of the needle 104 shrouded within the introducer 102 (i.e. with the needle 104 in the retracted position). Advancement of the introducer 102 can be stopped when the introducer 102 is in contact with the pericardium. Fluoroscopy can be used to confirm the position of the introducer 102 and/or the sharp distal tip 132. The handle 134 of the actuator 106 can then be rotated in a first direction about the longitudinal axis 108, to puncture the pericardium with the needle 104. Rotation of the handle 134 can be achieved manually or electronically. As described above, rotation of the handle 134 causes rotation of the lead screw 136 of the actuator 106, and rotation of the lead screw 136 causes advancement the needle 104. As the needle 104 advances, the sharp distal tip 132 of the needle 104 advances out of the introducer 102, and punctures the pericardium. Rotation of the handle 134 can be stopped, for example, after a set number of turns. Alternatively, the device 100 can be configured so that the handle 134 can be rotated only by a set amount. One the pericardium has been punctured and the epicardium has been accessed, a secondary medical procedure can be carried out (e.g. epicardial ablation).

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A pericardial puncture device comprising:
    an introducer extending along a longitudinal axis between an introducer proximal portion defining an introducer proximal end and an introducer distal portion defining an introducer distal end, wherein the introducer has an introducer lumen extending between the introducer proximal end and the introducer distal end;
    a needle received in the introducer lumen and extending between a needle proximal portion and a needle distal portion having a sharp distal tip, wherein the needle is movable from a retracted configuration to an advanced configuration, wherein in the retracted configuration the sharp distal tip is within the introducer lumen and shy of the introducer distal end, and wherein in the advanced configuration the sharp distal tip is outside of the introducer lumen and proud of the introducer distal end;
    an actuator mounted to the introducer proximal portion and engaged with the needle proximal portion, wherein the actuator comprises a handle that is rotatable in a first direction with respect to the introducer to drive movement of the needle from the retracted configuration towards the advanced configuration, and wherein the handle is further rotatable in a second direction with respect to the introducer to drive movement of the needle from the advanced configuration towards the retracted configuration, wherein the actuator comprises a lead screw mounted to the handle, wherein the lead screw is received in the introducer proximal portion and the handle extends proud of the introducer proximal portion, and wherein rotation of the handle in the first direction drives rotation of the lead screw in the first direction, wherein the needle proximal portion comprises a lead nut; and the lead screw is received in and engaged with the lead nut to drive movement of the needle from the retracted configuration to the advanced configuration by rotation of the handle.

2. The pericardial puncture device of claim 1, wherein the handle is rotatable about the longitudinal axis of the introducer.

3. The pericardial puncture device of claim 1, wherein the actuator is longitudinally fixed with respect to the introducer.

4. The pericardial puncture device of claim 1, wherein at least a section of the introducer distal portion is radiopaque.

5. The pericardial puncture device of claim 1, wherein the introducer distal end is blunt.

6. The pericardial puncture device of claim 1, wherein:
    the introducer proximal portion comprises an internal circumferential groove;
    the handle comprises an outer circumferential tongue; and
    the outer circumferential tongue is received in the internal circumferential groove to longitudinally fix the actuator with respect to the introducer.

7. The pericardial puncture device of claim 1, wherein the introducer comprises a metallic hypotube embedded in a polymeric shaft.

8. The pericardial puncture device of claim 7, wherein the metallic hypotube is a stainless steel hypotube and the polymeric shaft is a high-density polyethylene shaft.

9. The pericardial puncture device of claim 1, wherein the introducer has a length of at least 5 inches.

10. The pericardial puncture device of claim 1, wherein the needle is of a one-piece construction.

11. The pericardial puncture device of claim 10, wherein the needle is fabricated from stainless steel.

12. A pericardial puncture device comprising:

an introducer extending along a longitudinal axis between an introducer proximal portion defining an introducer proximal end and an introducer distal portion defining an introducer distal end, wherein the introducer has an introducer lumen extending between the introducer proximal end and the introducer distal end;

an actuator mounted to the introducer, wherein the actuator comprises a lead screw that is received in the introducer proximal portion and a handle that extends proud of the introducer proximal portion, wherein the actuator is rotatable about the longitudinal axis with respect to the introducer and is longitudinally fixed with respect to the introducer;

a needle extending along the longitudinal axis between a needle proximal portion having a lead nut and a needle distal portion having a sharp distal tip, wherein the lead screw is received in and engaged with the lead nut, and wherein rotation of the actuator about the longitudinal axis in a first direction drives longitudinal advancement of the needle to position the sharp distal tip proud of the introducer distal end, and wherein rotation of the actuator about the longitudinal axis in a second direction opposite the first direction drives longitudinal retraction of the needle to position the sharp distal tip shy of the introducer distal end.

13. A puncture device comprising:

an introducer extending along a longitudinal axis between an introducer proximal portion defining an introducer proximal end and an introducer distal portion defining an introducer distal end, wherein the introducer has an introducer lumen extending between the introducer proximal end and the introducer distal end and the introducer proximal portion comprises an internal circumferential groove;

a needle received in the introducer lumen and extending between a needle proximal portion and a needle distal portion having a sharp distal tip, wherein the needle is movable from a retracted configuration to an advanced configuration, wherein in the retracted configuration the sharp distal tip is within the introducer lumen and shy of the introducer distal end, and wherein in the advanced configuration the sharp distal tip is outside of the introducer lumen and proud of the introducer distal end;

an actuator mounted to the introducer proximal portion and engaged with the needle proximal portion, wherein the actuator comprises a handle that is rotatable in a first direction with respect to the introducer to drive movement of the needle from the retracted configuration towards the advanced configuration, wherein the handle comprises an outer circumferential tongue and the outer circumferential tongue is received in the internal circumferential groove to longitudinally fix the actuator with respect to the introducer, wherein the actuator comprises a lead screw mounted to the handle, wherein the lead screw is received in the introducer proximal portion and the handle extends proud of the introducer proximal portion, and wherein rotation of the handle in the first direction drives rotation of the lead screw in the first direction, wherein the needle proximal portion comprises a lead nut; and the lead screw is received in and engaged with the lead nut to drive movement of the needle from the retracted configuration to the advanced configuration by rotation of the handle.

14. The puncture device of claim 13, wherein the introducer distal portion includes a radiopaque band.

15. The puncture device of claim 13, wherein the introducer comprises a hypotube embedded in a polymeric shaft.

* * * * *